(12) United States Patent
Nakamura et al.

(10) Patent No.: US 10,603,096 B2
(45) Date of Patent: Mar. 31, 2020

(54) TREATMENT-ENERGY APPLYING STRUCTURE AND MEDICAL TREATMENT DEVICE

(71) Applicant: Olympus Corporation, Hachioji-shi, Tokyo (JP)

(72) Inventors: Kotaro Nakamura, Hino (JP); Shinji Yasunaga, Higashimurayama (JP)

(73) Assignee: Olympus Corporation, Tokyo (JP)

( * ) Notice: Subject to any disclaimer, the term of this patent is extended or adjusted under 35 U.S.C. 154(b) by 377 days.

(21) Appl. No.: 15/673,715

(22) Filed: Aug. 10, 2017

(65) Prior Publication Data

US 2017/0333108 A1    Nov. 23, 2017

Related U.S. Application Data

(63) Continuation of application No. PCT/JP2015/054492, filed on Feb. 18, 2015.

(51) Int. Cl.
*A61B 18/04* (2006.01)
*A61B 18/08* (2006.01)
(Continued)

(52) U.S. Cl.
CPC ............ *A61B 18/085* (2013.01); *A61B 18/04* (2013.01); *A61B 18/1445* (2013.01);
(Continued)

(58) Field of Classification Search
CPC ... A61B 18/04; A61B 18/085; A61B 18/1445; A61B 2018/00095; A61B 2018/00619; A61B 2018/00994
See application file for complete search history.

(56) References Cited

U.S. PATENT DOCUMENTS

2009/0112200 A1 * 4/2009 Eggers ............... A61B 17/3211
606/29
2011/0077630 A1 * 3/2011 Tanaka ................ A61B 18/085
606/29
(Continued)

FOREIGN PATENT DOCUMENTS

JP     2006-158517     6/2006
JP     2014-124491     7/2014
JP     2014-144183     8/2014

OTHER PUBLICATIONS

English Translation of International Search Report and Written Opinion dated May 26, 2015 issued in PCT/JP2015/054492, 6 pages.

*Primary Examiner* — Daniel W Fowler
(74) *Attorney, Agent, or Firm* — Matthew M. Eslami (57) ABSTRACT

A treatment-energy applying structure includes a flexible substrate having a wiring pattern having a heat-generation region and a connection region. A heat transfer plate faces a surface of the flexible substrate, and transfers heat to a body tissue. An adhesive sheet, having heat conductivity, is disposed between the flexible substrate and the heat transfer plate to cover the entirety of the heat-generation region and the heat transfer plate. A region of the adhesive sheet protrudes from the heat transfer plate to cover a region of the connection region. A pair of lead wires connects to the connection region outside of the covered region. The adhesive sheet is longer than the heat transfer plate and shorter than the flexible substrate. A gap between an end of the heat transfer plate and the lead wires is longer than a diameter of the lead wires or a thickness of the heat transfer plate.

14 Claims, 4 Drawing Sheets

(51) Int. Cl.
    *A61B 18/14*     (2006.01)
    *A61B 17/00*     (2006.01)
    *A61B 18/00*     (2006.01)
    *A61N 7/02*     (2006.01)

(52) U.S. Cl.
    CPC ............... *A61B 2017/00017* (2013.01); *A61B 2017/00973* (2013.01); *A61B 2018/00095* (2013.01); *A61B 2018/00619* (2013.01); *A61B 2018/00994* (2013.01); *A61N 7/02* (2013.01)

(56) References Cited

U.S. PATENT DOCUMENTS

| | | | |
|---|---|---|---|
| 2013/0253508 A1* | 9/2013 | Ide | A61B 18/085 606/41 |
| 2015/0289922 A1 | 10/2015 | Yasunaga | |
| 2015/0327909 A1 | 11/2015 | Nakamura | |
| 2017/0215938 A1 | 8/2017 | Yasunaga | |

* cited by examiner

TREATMENT-ENERGY APPLYING STRUCTURE AND MEDICAL TREATMENT DEVICE

CROSS-REFERENCE TO RELATED APPLICATION(S)

This application is a continuation application of PCT Application No. PCT/JP2015/054492 filed Feb. 18, 2015, which is hereby incorporated by reference in its entirety.

TECHNICAL FIELD

The present invention relates to treatment-energy applying structures and medical treatment devices.

BACKGROUND

Conventional medical treatment devices have been known which comprise a treatment-energy applying structure to apply energy to a body tissue and treat (e.g., junction or anastomose) the body tissue by the energy applied.

A conventional treatment-energy applying structure comprises a treatment member made of metal having high heat conductivity, for example, a thin-film resistor and an electrode disposed at the treatment member, and a lead wire to be connected to the electrode. Electricity is applied to the thin-film resistor through the lead wire and the electrode, whereby the treatment member is heated. Then thermal energy is applied to a body tissue that is in contact with the treatment member.

SUMMARY

The present invention provides a treatment-energy applying structure. In one aspect the system comprises a flexible substrate having one surface including a wiring pattern. The wiring pattern comprises a heat-generation region configured to generate heat when electricity is applied to the heat-generation region and a connection region that has electrical continuity with the heat-generation region. A heat transfer plate is disposed so as to face the one surface of the flexible substrate. The heat transfer plate is configured to contact a body tissue and transfer heat from the heat-generation region to the body tissue. An adhesive sheet is disposed between the flexible substrate and the heat transfer plate so as to cover the entirety of the heat-generation region and the entirety of the heat transfer plate to adhere the flexible substrate to the heat transfer plate. The adhesive sheet has a protrusion region that protrudes from the heat transfer plate to cover a covered region of the connection region. The adhesive sheet has heat conductivity. A pair of lead wires connects to the connection region outside of the covered region.

In another aspect the treatment-energy applying structure comprises a flexible substrate having one surface including a wiring pattern. The wiring pattern comprises a heat-generation region configured to generate heat when electricity is applied to the heat-generation region and a connection region that has electrical continuity with the heat-generation region. A heat transfer plate is disposed so as to face the one surface of the flexible substrate. The heat transfer plate is configured to contact a body tissue and transfer heat from the heat-generation region to the body tissue. An adhesive sheet is disposed between the flexible substrate and the heat transfer plate so as to cover the entirety of the heat transfer plate to adhere the flexible substrate to the heat transfer plate. The adhesive sheet has heat conductivity.

In another aspect the treatment-energy applying structure comprises a substrate having one surface including a wiring pattern. The wiring pattern comprises a heat-generation region configured to generate heat when electricity is applied to the heat-generation region and a connection region that has electrical continuity with the heat-generation region. A heat transfer plate is disposed so as to face the one surface of the substrate. The heat transfer plate is configured to contact a body tissue and transfer heat from the heat-generation region to the body tissue. A pair of lead wires connects to the connection region. There is a gap between an end of the heat transfer plate and the lead wires. The length of the gap is greater than a diameter of the lead wires and greater than a thickness of the heat transfer plate.

In another aspect the treatment-energy applying structure comprises a flexible substrate having one surface including a wiring pattern. The wiring pattern comprises a heat-generation region configured to generate heat when electricity is applied to the heat-generation region and a connection region that has electrical continuity with the heat-generation region. A heat transfer plate is disposed so as to face the one surface of the flexible board. The heat transfer plate being configured to contact a body tissue and transfer heat from the heat-generation region to the body tissue. An adhesive sheet is disposed between the flexible substrate and the heat transfer plate to adhere the flexible substrate to the heat transfer plate. The adhesive sheet has heat conductivity and a dimension in length that is longer than a dimension in length of the heat transfer plate and that is shorter than a dimension in length of the flexible board.

BRIEF DESCRIPTION OF THE DRAWINGS

Objects, features, and advantages of embodiments disclosed herein may be better understood by referring to the following description in conjunction with the accompanying drawings. The drawings are not meant to limit the scope of the claims included herewith. For clarity, not every element may be labeled in every Figure. The drawings are not necessarily to scale, emphasis instead being placed upon illustrating embodiments, principles, and concepts. Thus, features and advantages of the present disclosure will become more apparent from the following detailed description of exemplary embodiments thereof taken in conjunction with the accompanying drawings.

DETAILED DESCRIPTION

Traditional treatment-energy applying structures are configured so that the lead wire comes in contact with the treatment member via the electrode, and therefore heat at the treatment member easily flows into the lead wire. That is, the temperature of the treatment member around where the electrode is connected to the lead wire easily drops. This causes non-uniformity of the temperature of the treatment member, which causes non-uniformity of the temperature of a treatment surface of the treatment member that is in contact with a body tissue as well, and therefore the body tissue may fail to receive thermal energy uniformly.

The following describes one embodiment of the present invention, with reference to the drawings. The present invention is not limited to the embodiment described below. Referring to the drawings, like numbers indicate like components throughout the drawings.

According to the present invention, it is possible to provide the treatment-energy applying structure and the medical treatment device that have an advantageous effect of applying thermal energy to a body tissue to be treated uniformly.

Figure 1:
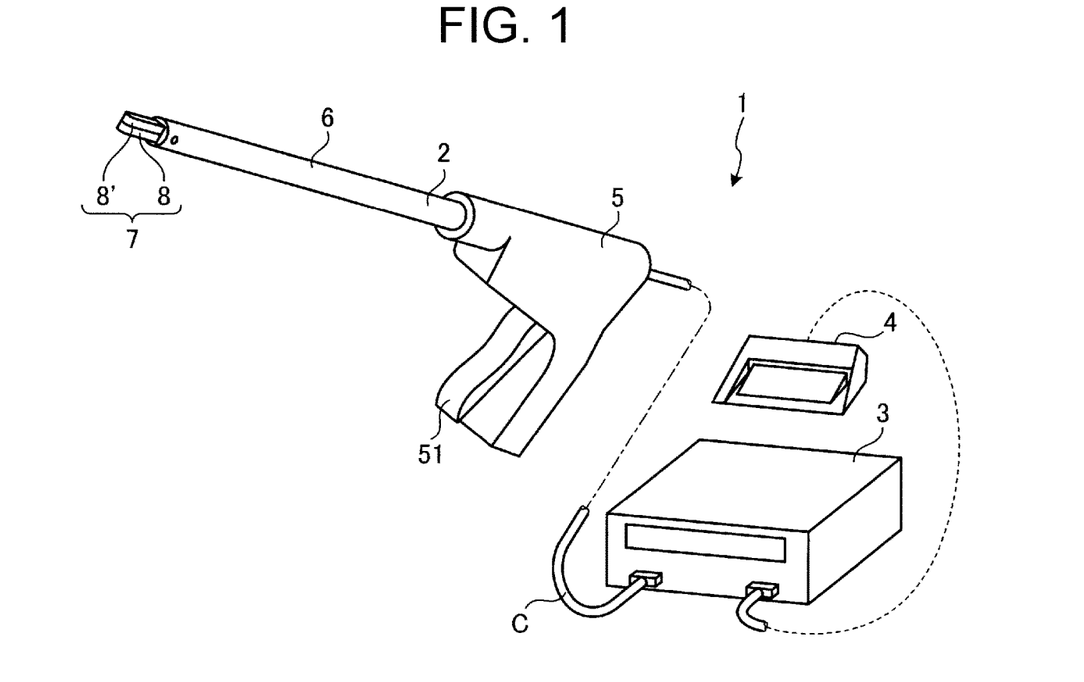
FIG. 1 schematically shows a medical treatment system according to one embodiment of the present invention.

FIG. 1 schematically shows a medical treatment system 1 according to one embodiment of the present invention.

The medical treatment system 1 is configured to apply energy to a body tissue to be treated so as to treat the body tissue (e.g., junction or anastomose). As shown in FIG. 1, this medical treatment system 1 comprises a medical treatment device 2, a controller 3 and a foot switch 4.

The medical treatment device 2 may be a linear-type tool for surgical treatment to treat a body tissue through an abdominal wall, for example. As shown in FIG. 1, this medical treatment device 2 comprises a handle 5, a shaft 6 and a grasper 7.

The handle 5 is a part that may be gripped by an operator. This handle 5 has a lever 51 as shown in FIG. 1.

As shown in FIG. 1, the shaft 6 has a substantially circular cylindrical shape, and has one end connected to the handle 5. To the other end of the shaft 6, the grasper 7 is attached. This shaft 6 internally comprises an opening/closing mechanism (not illustrated) configured to open and close jaws 8, 8' (FIG. 1) making up the grasper 7 in response to the manipulation of the lever 51 by the operator. The shaft 6 internally comprises an electric cable C (FIG. 1) as well that is connected to a controller 3 via the handle 5, and the electric cable C is disposed from one end to the other end of the shaft.

Figure 2:
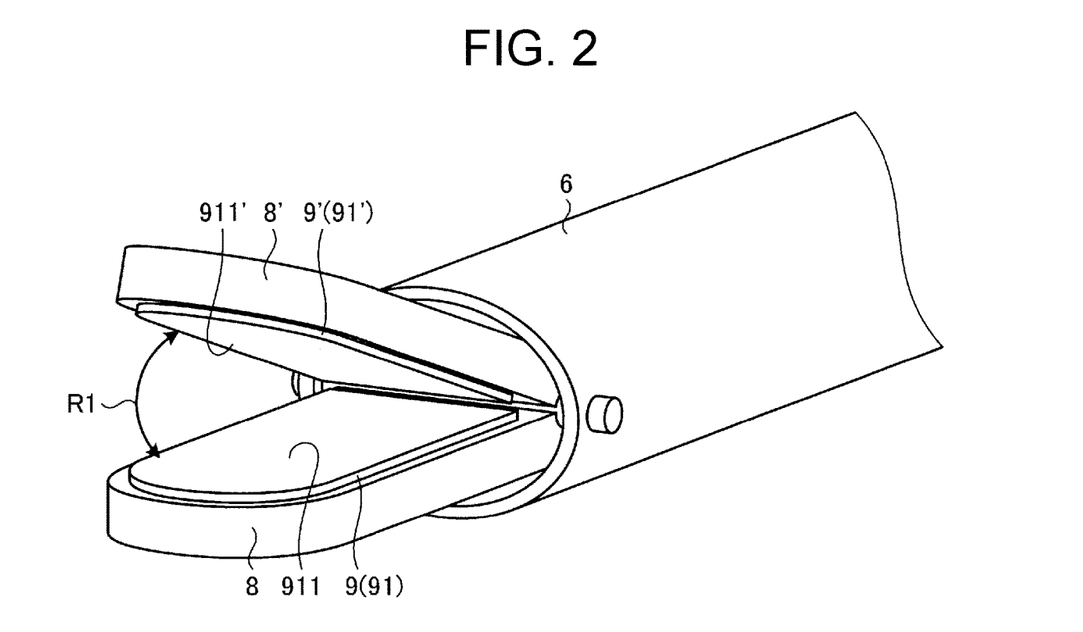
FIG. 2 is an enlarged view of the distal end part of the medical treatment device in FIG. 1.

FIG. 2 is an enlarged view of the distal end part of the medical treatment device 2.

In FIGS. 1 and 2, an element denoted with a numeral without "'" (prime) has the same structure as that of an element denoted with the numeral with "'" (prime). The same applies to the following drawings.

The grasper 7 is to grasp a body tissue for treatment. As shown in FIG. 1 or 2, this grasper 7 comprises a pair of jaws 8, 8'.

The pair of jaws 8, 8' is pivotally supported at the other end of the shaft 6 so as to be openable and closable in the direction of arrow R1 (FIG. 2), and is capable of grasping a body tissue in accordance with the manipulation of the lever 51 by the operator.

As shown in FIG. 2, the pair of jaws 8 and 8' comprises the treatment-energy applying structures 9 and 9', respectively.

Since the treatment-energy applying structures 9 and 9' as the pair has the same structure, the following describes the treatment-energy applying structure 9 only.

Figure 3:
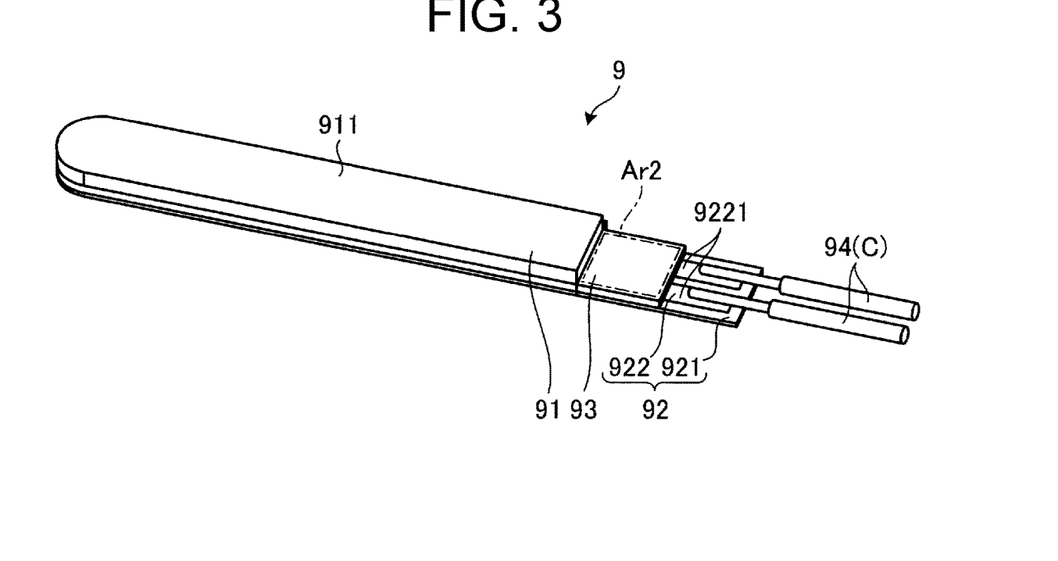
FIG. 3 shows the treatment-energy applying structure in FIG. 2.
Figure 4:
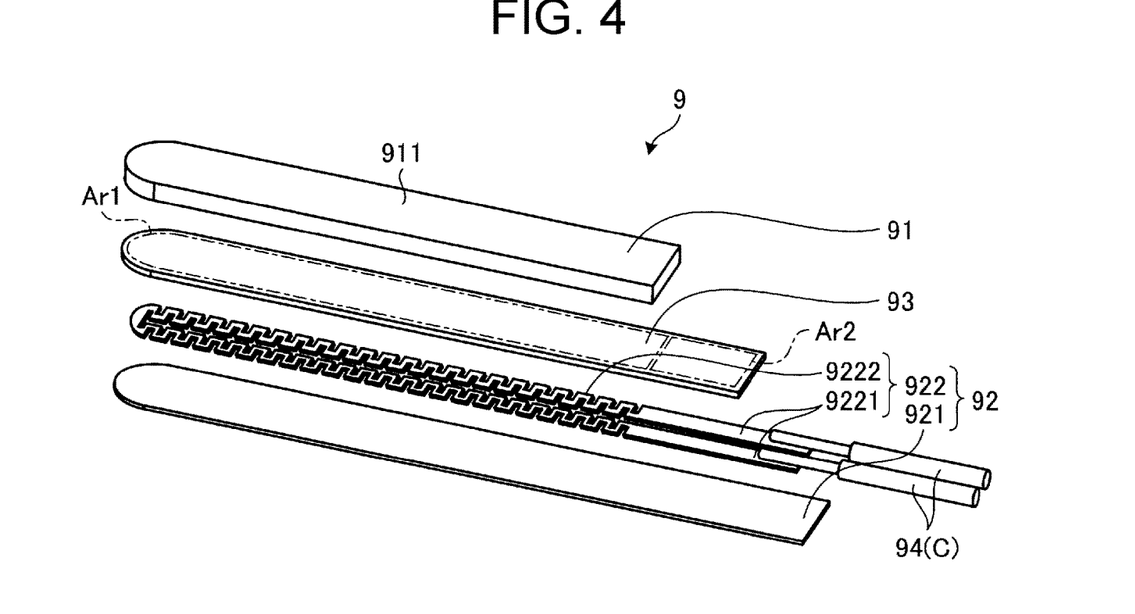
FIG. 4 shows the treatment-energy applying structure in FIG. 2.

FIGS. 3 and 4 show the treatment-energy applying structure 9. Specifically, FIG. 3 is a perspective view of the treatment-energy applying structure 9 viewed from the above in FIG. 2. FIG. 4 is an exploded perspective view of FIG. 3.

The treatment-energy applying structure 9 is attached to the upper surface of the lower jaw 8 in FIGS. 1 and 2. The treatment-energy applying structure 9 applies thermal energy to a body tissue under the control by the controller 3. As shown in FIG. 3 or 4, this treatment-energy applying structure 9 comprises a heat transfer plate 91, a flexible board (substrate) 92, an adhesive sheet 93 and two lead wires 94.

The heat transfer plate 91 comprises a long thin plate made of copper, for example. When the treatment-energy applying structure 9 is attached to the jaw 8, a treatment surface 911 as one of the surfaces of the heat transfer plate is directed toward the jaw 8' (upward in FIGS. 1 and 2). The treatment surface 911 of the heat transfer plate 91 comes in contact with a body tissue grasped between the jaws 8, 8', and transfers heat from the flexible board 92 to the body tissue (applies thermal energy to the body tissue).

The flexible board 92 functions as a sheet heater at a part of which generates heat, and heats the heat transfer plate 91 with the generated heat. As shown in FIG. 3 or 4, this flexible board 92 comprises a substrate 921 and a wiring pattern 922.

The substrate 921 may be a long sheet made of an insulating material, such as polyimide.

The substrate 921 may have a dimension in width that is substantially the same as a dimension in width of the heat transfer plate 91. The substrate 921 may have a dimension in length (the dimension in horizontal length in FIG. 4) that is longer than a dimension in length (the dimension in horizontal length in FIG. 4) of the heat transfer plate 91.

The wiring pattern 922 may be prepared by bonding to one of the surfaces of the substrate 921 or by processing a metal film that is vapor-deposited to one of the surfaces of the substrate 921, and is used for heating the heat transfer plate 91. As shown in FIG. 3 or 4, this wiring pattern 922 may have a pair of lead wire connecting parts (connection regions) 9221 and an electrical-resistance pattern (heat-generation region) 9222 (FIG. 4).

The wiring pattern 922 may be made of stainless steel or platinum, for example.

The pair of lead wire connecting parts 9221 may extend from one end part (the right end, or proximal, part in FIG. 4) of the substrate 921 toward the other end part (the left end, or distal, part in FIG. 4), and may be disposed so that the lead wire connecting parts face each other along the width direction of the substrate 921. The pair of lead wire connecting parts 9221 may be joined (connected) to two lead wires 94 of the electric cable C (see FIG. 4), respectively. The pair of lead wire connecting parts 9221 may correspond to a connection region of the present invention.

The electrical-resistance pattern 9222 may have one end connected (establishing electrical continuity) to one of the lead wire connecting parts 9221, may have a U-letter shape following the outer edge of the substrate 921 starting from the one end, and may have the other end connected (establishing electrical continuity) to the other of the lead wire connecting parts 9221. The electrical-resistance pattern 9222 generates heat by applying voltage (electricity) to the pair of lead wire connecting parts 9221 from the controller 3 via the two lead wires 94. The electrical-resistance pattern 9222 may correspond to a heat-generation region of the present invention.

The adhesive sheet 93 may be inserted between the heat transfer plate 91 and the flexible board 92 (FIGS. 3 and 4), and is to bond (or adhere) and fix the heat transfer plate 91 to the flexible board 92 while protruding a part of the flexible board 92 from the heat transfer plate 91. This adhesive sheet 93 may be a long sheet having good heat conductivity and insulation properties, may be resistant to high temperatures, and has adhesiveness, and may be formed by mixing ceramic having high heat conductivity, such as alumina or aluminum nitride with epoxy resin, for example.

The adhesive sheet 93 may have a dimension in width that is substantially the same as a dimension in width of the heat transfer plate 91 and the substrate 921. The adhesive sheet 93 may have a dimension in length (the dimension in horizontal length in FIG. 4) that is longer than a dimension in length (the dimension in horizontal length in FIG. 4) of the heat transfer plate 91 and is shorter than a dimension in length (the dimension in horizontal length in FIG. 4) of the substrate 921.

Figure 5:
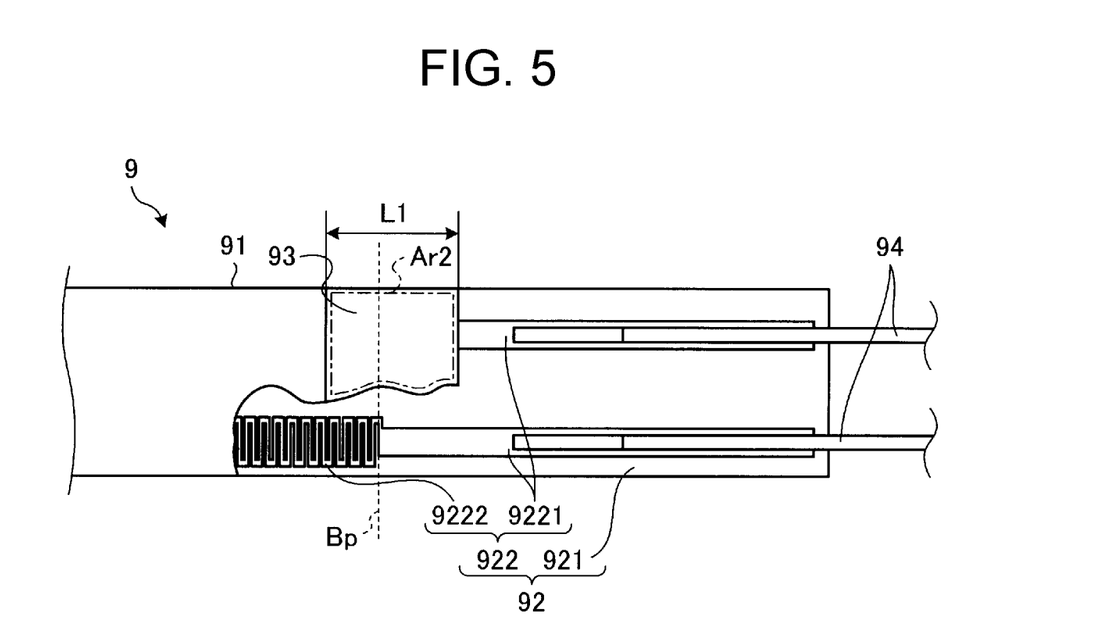
FIG. 5 shows the positional relationship among the heat transfer plate, the flexible board, the adhesive sheet and the two lead wires when the treatment-energy applying structure shown in FIGS. 3 and 4 are assembled.
Figure 6:
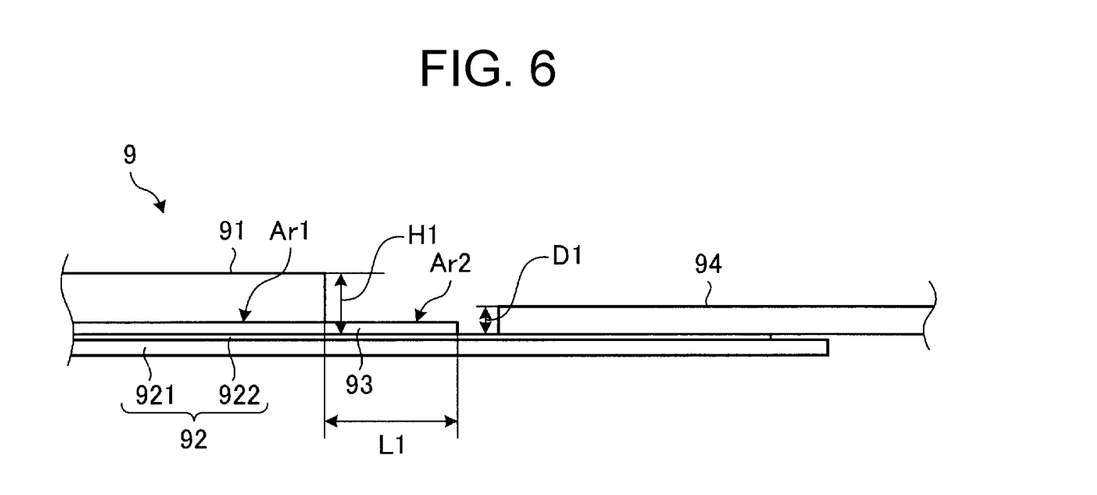
FIG. 6 shows the positional relationship among the heat transfer plate, the flexible board, the adhesive sheet and the two lead wires when the treatment-energy applying structure shown in FIGS. 3 and 4 are assembled.

Referring next to FIGS. 5 and 6, the positional relationship among the elements 91 to 94 in the assembled treatment-energy applying structure 9 is described below.

FIGS. 5 and 6 describe the positional relationship among the heat transfer plate 91, the flexible board 92, the adhesive sheet 93 and the two lead wires 94 in the assembled treatment-energy applying structure 9. Specifically, FIG. 5 is an enlarged plan view of a part of the treatment-energy applying structure 9. FIG. 5 omits a part of the adhesive sheet 93. FIG. 6 is an enlarged side view of a part of the treatment-energy applying structure 9.

As shown in FIG. 5, the adhesive sheet 93 bonds and fixes the heat transfer plate 91 and the flexible board 92 while protruding a part of the electrical-resistance pattern 9222 and the pair of lead wire connecting parts 9221 as a whole from the heat transfer plate 91. That is, as shown in FIG. 5, the boundary position Bp between the electrical-resistance pattern 9222 and the pair of lead wire connecting parts 9221 is outside of the heat transfer plate 91 when viewed along the longitudinal direction of the adhesive sheet 93.

The adhesive sheet 93 has two regions including a first region Ar1 and a second region Ar2. In Ar1 (FIGS. 4 and 6), when the adhesive sheet 93 is inserted between the heat transfer plate 91 and the flexible board 92, the adhesive sheet 93 covers the entire of the heat transfer plate 91 and a part of the electrical-resistance pattern 9222, and Ar2 (FIGS. 3 to 6) is the region protruding from the heat transfer plate 91 to the right in FIGS. 5 and 6, and covers a part of the electrical-resistance pattern 9222 and a part of the pair of lead wire connecting parts 9221 (i.e. covered region) across the boundary position Bp. That is, the second region Ar2 is a protrusion region of the present invention.

The second region Ar2 may have a dimension in length L1 (the dimension in horizontal length in FIGS. 5 and 6) set as follows.

Specifically, the dimension in length L1 may be larger than a dimension in thickness of the of the heat transfer plate 93. The dimension in length L1 may be larger than a dimension in height H1 (a total of a dimension in thickness of the adhesive sheet 93 and a dimension in thickness of the heat transfer plate 91 in FIG. 6). The dimension in length L1 may be larger than a dimension of the size D1 of the lead wire, or lead wires, 94, that is the diameter or thickness of the lead wire, or lead wires 94 (FIG. 6). Typically, the two lead wires 94 may have the same size D1, or diameter. In this configuration, as shown in FIG. 6, there may be a gap between the end of the heat transfer plate 91 and the end of each of the lead wires 94. As shown in FIG. 6, typically the lead wires may terminate at the same position, therefore there may be a single gap between the end of the heat transfer plate 91 and both lead wires 94. The gap may be longer than the length L1 of second region Ar2. The gap may be longer than the thickness of the heat transfer plate, or the gap may be longer than the size D1 of the lead wire, or lead wires 94.

As shown in FIGS. 5 and 6, the two lead wires 94 are connected at a position of the pair of lead wire connecting parts 9221 where the lead wires do not come in contact with the heat transfer plate 91 and the adhesive sheet 93 (the position other than the second region Ar2, i.e. within the connection region but outside the covered region).

The foot switch 4 is a part that the operator manipulates with the foot. In response to the manipulation of the foot switch 4, electricity from the controller 3 to the medical treatment device 2 (the electrical-resistance pattern 9222) may be turned on and off.

Such means for switching on and off is not limited to the foot switch 4, and other switches manipulated by a hand, for example, may be used.

The controller 3 comprises a CPU (Central Processing Unit) or the like, and controls the operation of the medical treatment device 2 as a whole in accordance with a predetermined control program. Specifically, the controller 3 may be configured to apply voltage to the electrical-resistance pattern 9222 via the electric cable C (the two lead wires 94) in response to the manipulation of the foot switch 4 (manipulation of turning on) by the operator, so as to heat the heat transfer plate 91.

Next, the following describes the operation (activation method) of the medical treatment system 1 described above.

The operator may grip the medical treatment device 2 and inserts the distal end part (a part of the grasper 7 and the shaft 6) of the medical treatment device 2 into the abdominal cavity through the abdominal wall, for example. Then, the operator may manipulate the lever 51 to grasp a body tissue to be treated between the jaws 8, 8'.

Next, the operator may manipulate the foot switch 4 to turn electricity from the controller 3 to the medical treatment device 2 on. When electricity is turned on, the controller 3 applies voltage to the wiring pattern 922 via the electric cable C (the two lead wires 94), so as to heat the heat transfer plate 91. Then, the body tissue in contact with the heat transfer plate 91 is heated by heat of the heat transfer plate 91 for treatment.

The treatment-energy applying structure 9 according to the present embodiment as described above comprises the adhesive sheet 93 having good heat conductivity. The adhesive sheet 93 has the first region Ar1 that covers the entire of the heat transfer plate 91 and a part of the electrical-resistance pattern 9222. This can transfer heat of the electrical-resistance pattern 9222 to the heat transfer plate 91 through the adhesive sheet 93, and therefore the heat transfer plate 91 can be heated reliably.

The two lead wires 94 may be connected at a position of the pair of lead wire connecting parts 9221 where the lead wires do not come in contact with the heat transfer plate 91 and the adhesive sheet 93 (the position other than the second region Ar2). That is, the treatment-energy applying structure 9 according to the present embodiment has a structure to prevent heat of the heat transfer plate 91 from flowing into the lead wires 94. Therefore, there is no part of locally temperature dropping at the heat transfer plate 91, and the temperature of the treatment surface 911 can be made uniform.

In this way, the treatment-energy applying structure 9 according to the present embodiment has an advantageous effect of applying thermal energy to a body tissue uniformly. Such a treatment-energy applying structure 9 can heat the heat transfer plate 91 to a desired temperature in a short time as compared with the conventional structure.

In the treatment-energy applying structure 9 according to the present embodiment, the boundary position Bp between the electrical-resistance pattern 9222 and the pair of lead wire connecting parts 9221 is located outside of the heat transfer plate 91 when viewed along the longitudinal direction of the adhesive sheet 93. Therefore, heat of the electrical-resistance pattern 9222 can be transferred to the end of the heat transfer plate 91 (the right end in FIG. 5 or 6) as well through the adhesive sheet 93, and therefore a body tissue at the end of the heat transfer plate 91 also can receive thermal energy uniformly like the other region.

Figure 7:
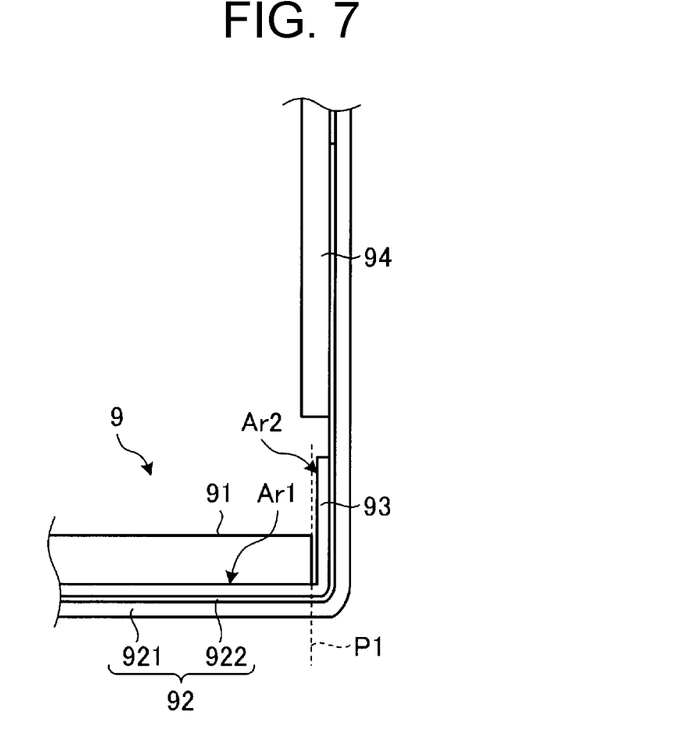
FIG. 7 explains an advantageous effect of one embodiment of the present invention.
Figure 8:
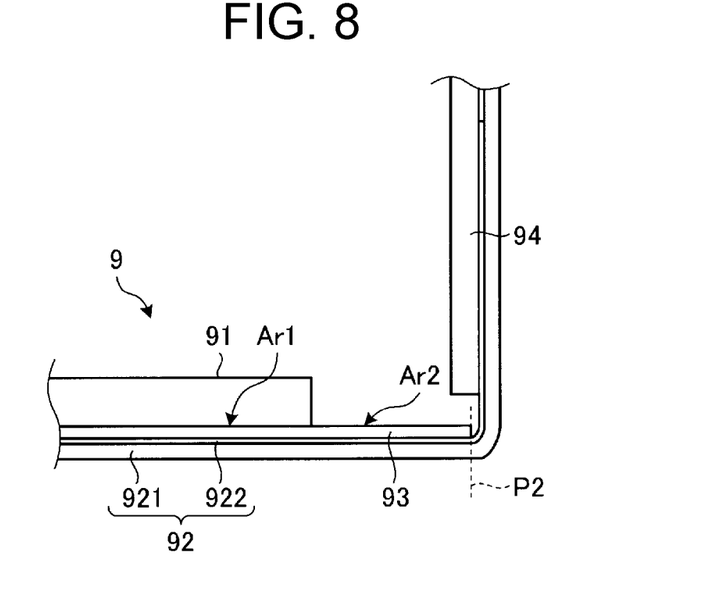
FIG. 8 explains an advantageous effect of one embodiment of the present invention.

FIGS. 7 and 8 explain the advantageous effect of the present embodiment. Specifically, FIGS. 7 and 8 correspond to FIG. 6.

In the treatment-energy applying structure 9 according to the present embodiment, the adhesive sheet 93 has good insulation properties. The adhesive sheet 93 has the second region Ar2, and the second region Ar2 may protrude from the heat transfer plate 91 and covers a part of the electrical-resistance pattern 9222 and a part of the pair of lead wire connecting parts 9221 across the boundary position Bp. The dimension in length L1 of the second region Ar2 may be set to be larger than the dimension that is largest between a dimension in height H1 at the right end of the heat transfer plate 91 in FIG. 5 or 6, a dimension in thickness of the heat transfer plate 91 and a dimension of the size D1 of the lead wire, or lead wires 94.

With this configuration, as shown in FIG. 7 or 8, when the treatment-energy applying structure 9 is bent during the use of the medical treatment device 2 (when the pair of jaws 8, 8' are opened and closed) at position P1 at the right end of the heat transfer plate 91 in FIG. 7 or at position P2 at the right end of the adhesive sheet 93 in FIG. 8, short circuit between the heat transfer plate 91 and the lead wires 94 (or the pair of lead wire connecting parts 9221) can be prevented.

That is the descriptions on one embodiment of the present invention, and the present invention is not limited only to the embodiment.

In the embodiment as stated above, the treatment-energy applying structures 9 and 9' are provided at the jaws 8 and 8', respectively, and this is not a limiting example. The treatment-energy applying structure may be provided at any one of the jaws 8, 8'.

In the embodiment as stated above, the treatment-energy applying structures 9 and 9' are configured to apply thermal energy to a body tissue, and high frequency energy or ultrasonic energy may be applied, instead of thermal energy.

In the embodiment as stated above, the heat transfer plate 91, the flexible board 92, and the adhesive sheet 93 have a flat-plate shape as stated above. This is not a limiting example, and they may have other flat-plate shape, and may have a U-letter shape in a plan view so as to secure the path along which a cutter moves, for example.

The invention claimed is:

1. A treatment-energy applying structure used in a medical treatment system, comprising:
   a flexible substrate having one surface including a wiring pattern thereon, the wiring pattern comprising:
      a heat-generation region configured to generate heat when electricity is applied to the heat-generation region; and
      a connection region connected to a pair of lead wires that has electrical continuity with the heat-generation region;
   a heat transfer plate disposed so as to face the one surface of the flexible substrate, the heat transfer plate configured to contact a body tissue and transfer heat from the heat-generation region to the body tissue; and
   an adhesive sheet disposed between the flexible substrate and the heat transfer plate so as to cover the entirety of the heat-generation region and the entirety of the heat transfer plate to adhere the flexible substrate to the heat transfer plate, the adhesive sheet having a protrusion region that protrudes from the heat transfer plate to cover a covered region of the connection region and the adhesive layer includes a laterally facing portion being exposed in a same direction that the connection region faces and an exposed portion of the connection region faces a side that the adhesive sheet being positioned; and wherein the adhesive sheet having heat conductivity and insulation properties to insulate the lead wires from the heat transfer plate.

2. The treatment-energy applying structure according to claim 1, wherein a boundary between the heat-generation region and the connection region is located outside of the heat transfer plate.

3. The treatment-energy applying structure according to claim 1, wherein the adhesive sheet has insulation properties, and a length of the protrusion region is larger than a total of a dimension in thickness of the adhesive sheet and a dimension in thickness of the heat transfer plate.

4. The treatment-energy applying structure according to claim 1, wherein the adhesive sheet has insulation properties and a length of the protrusion region is larger than a dimension in size of the lead wire.

5. A treatment-energy applying structure, comprising:
   a flexible substrate having one surface including a wiring pattern thereon, the wiring pattern comprising:
      a heat-generation region configured to generate heat when electricity is applied to the heat-generation region; and
      a connection region that has electrical continuity with the heat-generation region;
   a heat transfer plate disposed so as to face the one surface of the flexible substrate, the heat transfer plate being configured to contact a body tissue and transfer heat from the heat-generation region to the body tissue;
   an adhesive sheet disposed between the flexible substrate and the heat transfer plate so as to cover the entirety of the heat transfer plate to adhere the flexible substrate to the heat transfer plate, and the adhesive sheet having heat conductivity and wherein the adhesive layer includes a laterally facing portion being exposed in a same direction that the connection region faces and an exposed portion of the connection region faces a side that the adhesive sheet being positioned.

6. The treatment-energy applying structure according to claim 5, wherein a boundary between the heat-generation region and the connection region is located outside of the heat transfer plate.

7. The treatment-energy applying structure according to claim 5, wherein the adhesive sheet is configured so as to cover the entirety of the heat-generation region.

8. The treatment-energy applying structure according to claim 5, wherein
the adhesive sheet has insulation properties, and the adhesive sheet protrudes from the heat transfer plate to cover a covered region of the connection region, and
wherein a length of the adhesive sheet that protrudes from the heat transfer plate at the protrusion region where the adhesive sheet protrudes to the connection region is larger than a thickness of the heat transfer plate at an end of the heat transfer plate adjacent to the protrusion region.

9. The treatment-energy applying structure according to claim 5, further comprising a pair of lead wires connected to the connection region,
wherein the adhesive sheet has insulation properties, and the adhesive sheet protrudes from the heat transfer plate to cover a covered region of the connection region, and
wherein a length of the adhesive sheet that protrudes from the heat transfer plate at the protrusion region where the adhesive sheet protrudes to the connection region is larger than a dimension in size of the lead wires.

10. A treatment-energy applying structure, comprising:
a substrate having one surface including a wiring pattern thereon, the wiring pattern comprising:
a heat-generation region configured to generate heat when electricity is applied to the heat-generation region; and
a connection region that has electrical continuity with the heat-generation region;
a heat transfer plate disposed so as to face the one surface of the substrate, the heat transfer plate being configured to contact a body tissue and transfer heat from the heat-generation region to the body tissue;
a pair of lead wires connected to the connection region;
a gap between an end of the heat transfer plate and the lead wires;
wherein, a length of the gap is greater than a diameter of the lead wires, and
wherein, the length of the gap is greater than a thickness of the heat transfer plate; and
an adhesive sheet disposed between the flexible substrate and the heat transfer plate so as to cover the entirety of the heat transfer plate to adhere the flexible substrate to the heat transfer plate and wherein the adhesive layer includes a laterally facing portion being exposed in a same direction that the connection region faces and an exposed portion of the connection region faces a side that the adhesive sheet being positioned.

11. The treatment-energy applying structure according to claim 10, wherein:
the adhesive sheet having heat conductivity and disposed between the substrate and the heat transfer plate to adhere the substrate to the heat transfer plate,
wherein an exposed length of the adhesive sheet protrudes from the heat transfer plate to the connection region.

12. The treatment-energy applying structure according to claim 11, wherein the exposed length of the adhesive sheet has a length dimension that is greater than the thickness of the heat transfer plate.

13. The treatment-energy applying structure according to claim 11, wherein the exposed length of the adhesive sheet has a length dimension that is greater than the diameter of the lead wires.

14. A treatment-energy applying structure used in a medical treatment system, comprising:
a flexible substrate having one surface including a wiring pattern thereon, the wiring pattern comprising:
a heat-generation region configured to generate heat when electricity is applied to the heat-generation region, and
a connection region that has electrical continuity with the heat-generation region;
a heat transfer plate disposed so as to face the one surface of the flexible substrate, the heat transfer plate being configured to contact a body tissue and transfer heat from the heat-generation region to the body tissue; and
an adhesive sheet disposed between the flexible substrate and the heat transfer plate to adhere the flexible substrate to the heat transfer plate and wherein the adhesive layer includes a laterally facing portion being exposed in a same direction that the connection region faces and an exposed portion of the connection region faces a side that the adhesive sheet being positioned, and
the adhesive sheet having heat conductivity and a dimension in length that is longer than a dimension in length of the heat transfer plate and that is shorter than a dimension in length of the flexible substrate.

* * * * *